US007914785B2

(12) United States Patent
Mella et al.

(10) Patent No.: US 7,914,785 B2
(45) Date of Patent: Mar. 29, 2011

(54) B-CELL DEPLETING AGENTS, LIKE ANTI-CD20 ANTIBODIES OR FRAGMENTS THEREOF FOR THE TREATMENT OF CHRONIC FATIGUE SYNDROME

(75) Inventors: Olav Mella, Olsvik (NO); Oystein Fluge, Morvik (NO)

(73) Assignee: Bergen Teknologieverforing AS, Bergen (NO)

( * ) Notice: Subject to any disclaimer, the term of this patent is extended or adjusted under 35 U.S.C. 154(b) by 161 days.

(21) Appl. No.: 12/348,024

(22) Filed: Jan. 2, 2009

(65) Prior Publication Data

US 2009/0196879 A1    Aug. 6, 2009

(51) Int. Cl.
*A01N 43/48* (2006.01)
*A61K 39/395* (2006.01)

(52) U.S. Cl. ............... 424/130.1; 424/155.1; 424/152.1; 424/135.1; 424/133.1; 514/249

(58) Field of Classification Search .......................... None
See application file for complete search history.

(56) References Cited

U.S. PATENT DOCUMENTS

| 3,773,919 | A | 11/1973 | Boswell et al. |
|---|---|---|---|
| 4,816,567 | A | 3/1989 | Cabilly |
| 4,861,579 | A | 8/1989 | Meyer |
| 5,229,275 | A | 7/1993 | Goroff |
| 5,545,807 | A | 8/1996 | Surani et al. |
| 5,565,332 | A | 10/1996 | Hoogenboom et al. |
| 5,567,810 | A | 10/1996 | Weis et al. |
| 5,571,894 | A | 11/1996 | Wels et al. |
| 5,587,458 | A | 12/1996 | King et al. |
| 5,589,369 | A | 12/1996 | Seidman et al. |
| 5,591,669 | A | 1/1997 | Krimpenfort |
| 5,595,721 | A | 1/1997 | Kaminski et al. |
| 5,641,870 | A | 6/1997 | Rinderknecht |
| 5,677,180 | A | 10/1997 | Robinson |
| 5,693,780 | A | 12/1997 | Newman et al. |
| 5,721,108 | A | 2/1998 | Robinson et al. |
| 5,736,137 | A | 4/1998 | Anderson et al. |
| 5,776,456 | A | 7/1998 | Anderson et al. |
| 5,843,398 | A | 12/1998 | Kaminski et al. |
| 5,843,439 | A | 12/1998 | Anderson et al. |

(Continued)

FOREIGN PATENT DOCUMENTS

EP            0 330 191 A2    2/1988

(Continued)

OTHER PUBLICATIONS

Center for Disease Control and Prevention, "Chronic Fatigue Syndrome: Causes" [online], last updated Oct. 15, 2010 [retrieved Nov. 1, 2010], Retrieved from internet<URL: http://www.cdc.gov/cfs/general/causes/index.html#>.*

(Continued)

*Primary Examiner* — Lorraine Spector
*Assistant Examiner* — Claire Kaufman
(74) *Attorney, Agent, or Firm* — Whitham Curtis Christofferson & Cook, PC

(57) ABSTRACT

The present invention relates in a first aspect to a B-cell depleting anti-CD20 antibody or a CD20-binding antibody fragment thereof for the treatment of chronic fatigue syndrome and myalgic encephalomyelitis. In particular, the present invention relates to the use of anti-CD20 monoclonal antibodies or fragments thereof which are preferably humanized for the treatment of chronic fatigue syndrome/myalgic encephalomyelitis in a subject afflicted with said disease.

14 Claims, 1 Drawing Sheet

U.S. PATENT DOCUMENTS

| | | | |
|---|---|---|---|
| 5,849,898 | A | 12/1998 | Seed et al. |
| 6,015,542 | A | 1/2000 | Kaminski et al. |
| 6,090,365 | A | 7/2000 | Kaminski et al. |
| 6,120,767 | A | 9/2000 | Robinson et al. |
| 6,171,586 | B1 | 1/2001 | Lam et al. |
| 6,194,551 | B1 | 2/2001 | Idusogie et al. |
| 6,224,866 | B1 | 5/2001 | Barbera-Guillem |
| 6,242,195 | B1 | 6/2001 | Idusogie et al. |
| 6,267,958 | B1 | 7/2001 | Andya et al. |
| 6,287,537 | B1 | 9/2001 | Kaminski et al. |
| 6,399,061 | B1 | 6/2002 | Anderson et al. |
| 6,410,391 | B1 | 6/2002 | Zelsacher |
| 6,455,434 | B1 | 9/2002 | Binkerd et al. |
| 6,528,624 | B1 | 3/2003 | Idusogie et al. |
| 6,538,124 | B1 | 3/2003 | Idusogie et al. |
| 6,565,827 | B1 | 5/2003 | Kaminski et al. |
| 6,652,852 | B1 | 11/2003 | Robinson et al. |
| 6,682,734 | B1 | 1/2004 | Anderson et al. |
| 2002/0004587 | A1 | 1/2002 | Miller et al. |
| 2002/0009427 | A1 | 1/2002 | Wolin |
| 2002/0012665 | A1 | 1/2002 | Hanna |
| 2002/0058029 | A1 | 5/2002 | Hanna |
| 2002/0128488 | A1 | 9/2002 | Yamakawa |
| 2002/0136719 | A1 | 9/2002 | Shenoy et al. |
| 2002/0197255 | A1 | 12/2002 | Anderson et al. |
| 2002/0197256 | A1 | 12/2002 | Grewal |
| 2003/0029181 | A1 | 2/2003 | Terauchi |
| 2003/0068664 | A1 | 4/2003 | Albitar et al. |
| 2003/0082172 | A1 | 5/2003 | Anderson et al. |
| 2003/0095963 | A1 | 5/2003 | Anderson et al. |
| 2003/0103971 | A1 | 6/2003 | Hariharan |
| 2003/0147885 | A1 | 8/2003 | Anderson et al. |
| 2003/0157108 | A1 | 8/2003 | Presta |
| 2003/0180292 | A1 | 9/2003 | Hanna et al. |
| 2003/0185796 | A1 | 10/2003 | Wolin et al. |
| 2003/0219818 | A1 | 11/2003 | Bohen et al. |

FOREIGN PATENT DOCUMENTS

| | | |
|---|---|---|
| EP | 0 332 865 A2 | 3/1988 |
| WO | WO 93/11161 | 6/1993 |
| WO | WO 93/16185 | 8/1993 |
| WO | WO 95/03770 | 2/1995 |
| WO | WO 00/09160 | 8/1998 |
| WO | WO 98/35036 | 8/1998 |
| WO | WO 98/56418 | 12/1998 |
| WO | WO 98/58964 | 12/1998 |
| WO | WO 99/22764 | 5/1999 |
| WO | WO 99/51642 | 10/1999 |
| WO | WO 00/20864 | 4/2000 |
| WO | WO 00/27428 | 5/2000 |
| WO | WO 00/27433 | 5/2000 |
| WO | WO 00/42072 | 7/2000 |
| WO | WO 00/44788 | 8/2000 |
| WO | WO 00/67795 | 11/2000 |
| WO | WO 00/67796 | 11/2000 |
| WO | WO 01/03734 A1 | 1/2001 |
| WO | WO 01/10460 A1 | 2/2001 |
| WO | WO 01/10461 A1 | 2/2001 |
| WO | WO 01/10462 A1 | 2/2001 |
| WO | WO 01/13945 A1 | 3/2001 |
| WO | WO 01/34194 A1 | 5/2001 |
| WO | WO 01/74388 A1 | 10/2001 |
| WO | WO 01/77342 A1 | 10/2001 |
| WO | WO 01/80884 A1 | 11/2001 |
| WO | WO 01/97858 A2 | 12/2001 |
| WO | WO 02/04021 A1 | 1/2002 |
| WO | WO 02/34790 A1 | 5/2002 |
| WO | WO 02/079255 A1 | 10/2002 |
| WO | WO 03/002607 A1 | 1/2003 |
| WO | WO 03/049694 A2 | 6/2003 |
| WO | WO 03/061694 A1 | 7/2003 |
| WO | WO 03/068821 A2 | 8/2003 |
| WO | WO 2004/035607 A2 | 4/2004 |

OTHER PUBLICATIONS

Nye, F., Letters to the editor: Chronic fatigue syndrome and myalgic encephalomyelitis: The 2007 guildelines from the National Institute of Clinical Excellence, J. Infection, 55:569-572, 2007.*

Lundell et al., Clinical activity of folinic acid in patients with chronic fatigue syndrome, Arznelm.-Forsch./Drug Res. 56(6):399-404, 2006.*

Lyall et al., A systematic review and critical evaluation of the immunology of chronic fatigue syndrome, J. Physchosomatic Res. 55:79-90, 2003.*

Prins et al., Chronic fatigue syndrome, The Lancet, 376:346-355, Jan. 28, 2006.*

Klimas, N., "Immunologic Abnormalities in Chronic Fatigue Syndrome", Journal of Clinical Microbiolgy, vol. 28, No. 6, 1990, pp. 1403-1410.

Robertson, et al., "Lyphocyte Subset Differences in Patients with Chronic Fatigue Syndrome, Multiple Sclerosis and Major Depression", Clinical and Experminental Immuology, vol. 141, 2005, pp. 326-332.

Eurpoean search report for EP 08000006.0, filed Jan. 2, 2008.

* cited by examiner

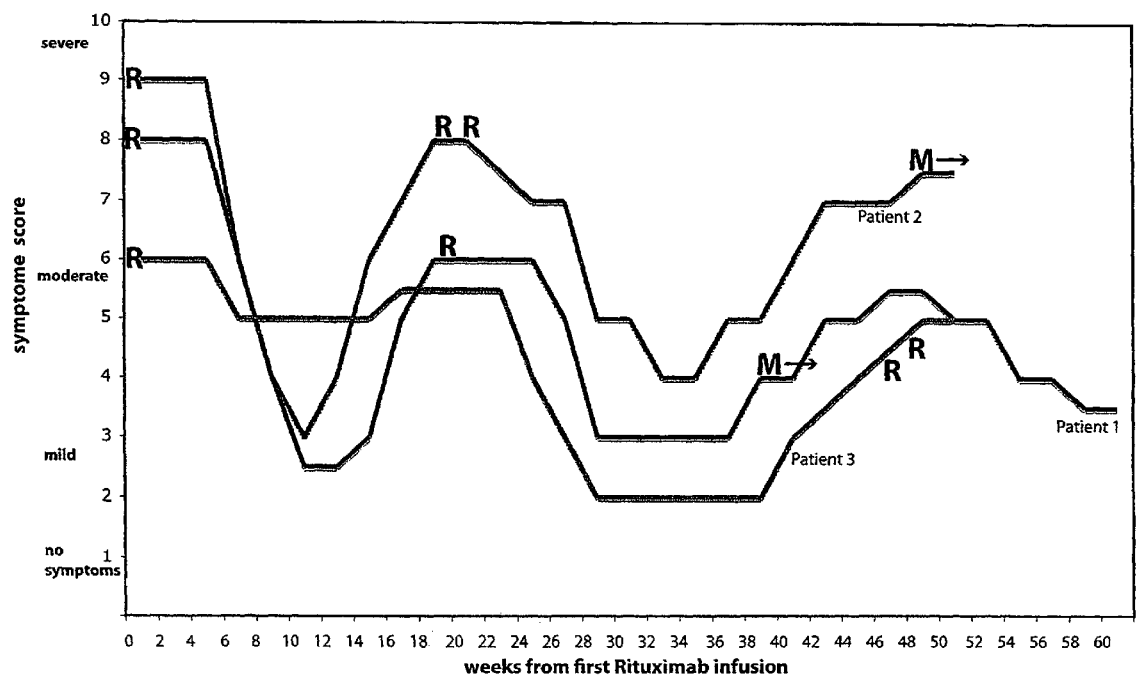

B-CELL DEPLETING AGENTS, LIKE ANTI-CD20 ANTIBODIES OR FRAGMENTS THEREOF FOR THE TREATMENT OF CHRONIC FATIGUE SYNDROME

The present invention relates in a first aspect to a B-cell depleting anti-CD20 antibody or a CD20-binding antibody fragment thereof for the treatment of chronic fatigue syndrome and myalgic encephalomyelitis. In particular, the present invention relates to the use of anti-CD20 monoclonal antibodies or fragments thereof which are preferably humanized for the treatment of chronic fatigue syndrome/myalgic encephalomyelitis in a subject afflicted with said disease.

In a further aspect, the present invention relates to B-cell depleting agents in general for the treatment of chronic fatigue syndrome and myalgic encephalomyelitis in a subject afflicted therewith.

TECHNICAL BACKGROUND

Chronic Fatigue Syndrome

Chronic Fatigue Syndrome (CFS) is characterized by an unexplained, severe fatigue, persisting for at least six consecutive months, and with a substantial reduction of previous levels in occupational, social, or personal activities. Also, the patients often experience persistent or recurrent symptoms such as impairment of short-term memory or concentration, muscle pain, joint pain without evidence of arthritis, headache, sleep disturbances, and post-exercise exhaustion (Fukuda K, et al., 1994, Ann Intern Med 121:953-9 et al 1994). Although many studies have shown subtle alterations in blood tests or radiological investigations, no biomarker or diagnostic test exists.

The prevalence of CFS worldwide is thought to be at least 0.5%, and the female:male ratio is 3:1 (Wyller V B. 2007, Acta Neurol Scand Suppl 187:7-14).

The aetiology of CFS remains unclear. The various hypotheses include immunological, virological, neuroendocrinological, and psychological mechanisms. The pathogenesis of CFS is presumed to be multifactorial and to involve both host and environmental factors (Devanur & Kerr 2006).

In a recent review of November 2007, describing current research priorities in CFS, the urgent need to elucidate the pathogenesis is highlighted (Kerr J R et al., 2007, J Clin Pathol 60:113-6).

Many patients suffering from CFS have a history of an acute viral infection preceding the development of fatigue. Although research data indicate evidence of immune system activation, the disease mechanisms remain unknown. A collaborative study group was formed in 2001; to elucidate the molecular mechanisms of CFS, with the aims to develop a diagnostic test and also to guide the development of more specific treatment (Devanur L D, Kerr J R. 2006, J Clin Virol 37:139-50).

Several gene expression studies have been performed in CFS, indicating that there are specific but complex gene alterations in accordance with a dysfunction in immune response and in defence mechanisms. One microarray study showed differential expression of 16 genes in CFS, suggesting T-cell activation and a disturbance of neuronal and mitochondrial function (Kaushik N, et. Al., 2005, J Clin Pathol 58:826-32). Another microarray study using serial samples of peripheral blood mononuclear cells total RNA, from patients developing CFS after Epstein Barr virus (EBV) infection and also from subjects with EBV infection without development of fatigue, concluded that several genes affecting mitochondrial function and cell cycle were deregulated (Vernon S D, et. Al., 2006, BMC Infect Dis 6:15). Another gene expression study in CFS suggested disturbance of exercise responsive genes including several involved in membrane transport and ion channels (Whistler T, et. al., 2005, BMC Physiol 5:5). Recently, an analysis of gene networks in CFS revealed seven distinct genomic subtypes with differences in clinical presentation and severity (Kerr J, et. al., 2007, J Clin Pathol). Several other studies have addressed global gene expression in CFS (Fang H, et. al., 2006, Pharmacogenomics 7:429-40; Whistler T, et al., 2003, J Transl Med 1:10).

The gene expression data are not conclusive, but suggests that there are gene expression disturbances in CFS representing various cellular functions, and may indicate that the disease has a heterogeneous pathogenesis.

A prevailing theme in CFS research has been a sustained immune deregulation, following acute exogenous stimuli such as a viral infection. Among the microbial pathogens reported to be associated with CFS are Epstein-Barr virus (Lerner A M, et al., 2004, In Vivo 18:101-6), enterovirus (Chia J K, Chia A Y. 2007, J Clin Pathol), parvovirus B19 (Matano S, et al., 2003, Intern Med 42:903-5), cytomegalovirus (Lerner A M, et al., 2002, In Vivo 16:153-9), human herpesvirus type 6 (Chapenko S, et al., 2006, J Clin Virol 37 Suppl 1:S47-51; Komaroff A L. 2006, J Clin Virol 37 Suppl 1:S39-46), Chlamydia pneumoniae (Nicolson G L, et al., 2003, Apmis 111:557-66). However, the data are not consistent (Soto N E, Straus S E., 2000, Herpes 7:46-50).

A recent study of postinfective fatigue syndrome found no differences in ex vivo cytokine production over a 12-month period, as compared to controls recovering promptly after infection (Vollmer-Conna U, et al., 2007, Clin Infect Dis 45:732-5). Others claim that despite evidence of immune activation, as demonstrated by increased number of activated T-cells and elevated levels of cytokines, the CFS patients may have a reduced immune cell function with a low NK-cell cytotoxicity and immunoglobulin deficiencies (Patarca R. 2001, Ann N Y Acad Sci 933:185-200).

Others reported a high number of circulating B-lymphocytes, altered NK-cells subsets also with increased expression of adhesion molecules, as compared to controls (Tirelli U, et al., 1994, Scand J Immunol 40:601-8), while another study showed reduced CD56+ NK-cells, and reduced CD4+ and CD8+ T-lymphocytes in CFS patients (Racciatti D, et al., 2004, Int J Immunopathol Pharmacol 17:57-62). Also, T- and NK-cells from CFS patients were found to express lower levels of the intracellular granule protein perforin, indicating a reduced ability to mediate cytotoxicity.

One study showed several abnormalities in laboratory markers associated with immune function in CFS patients (Klimas N G, et al., 1990, J Clin Microbiol 28:1403-10). The most consistent result was a low NK cell cytotoxicity, but also an increase in CD8+ T-cells, elevated number of CD20+ B-cells, and increase in the B-cell subset coexpressing CD20 and CD5 (Klimas et al 1990). These data were to some extent supported by a study reporting expansion of activated CD8+ cytotoxic T lymphocytes, along with a marked decrease in NK cell activity, in CFS patients (Barker E, et al., 1994. Clin Infect Dis 18 Suppl 1:S136-41).

A recent study comparing CFS patients and controls, reported decreased expression of CD69 on T-cells and NK-cells after mitogenic stimulation in vitro, indicating a disorder in the early activation of cellular immunity mediated by these cells (Mihaylova I, et al., 2007, Neuro Endocrinol Lett 28:477-83).

However, the data on immune deregulation in CFS are not consistent, and a study comparing lymphocyte subsets in CFS patients to those of patients with depression, multiple sclerosis and healthy controls, found no difference in T-, B-, or NK-cell subsets (Robertson M J, et al., 2005, Clin Exp Immunol 141:326-32). Similarly, a review of the immunology in CFS concluded that the studies performed in the research field had varying quality, and that no consistent pattern of immunological abnormalities could be identified (Lyall M, et al., 2003, J Psychosom Res 55:79-90).

Along with hypotheses of immune deregulation in CFS, autoimmunity to endogenous vasoactive neuropeptides has been proposed as a mechanism for the disease (Staines D R., 2005, Med Hypotheses 64:539-42), however not supported by scientific data. The author has also suggested a similar mechanisms in the aetiology of fibromyalgia, multiple sclerosis and amyotrophic lateral sclerosis, Parkinson's disease, and sudden infant death syndrome hypothesizing that autoimmunity against vasoactive neuropeptides acting as hormones, neurotransmitters, immunmodulators and neurotrophes may explain the complex clinical pictures of these diseases. However, no autoantibodies to these neuropeptides have been documented in CFS.

One study investigated the presence of circulating anti-muscle and anti-CNS antibodies in CFS patients and controls, with no detected pathogenic antibodies. Another report of antinuclear autoantibodies in CFS concluded that there was no association (Skowera A, et al., 2002, Clin Exp Immunol 129:354-8), while another investigating common autoantibodies and antibodies to neuron specific antigens showed higher rates of antibodies to microtubule-associated protein 2 and ssDNA in CFS (Vernon S D, Reeves W C. 2005, J Autoimmune Dis 2:5). A single study showed the presence of autoantibodies to muscarinic cholinergic receptor in a subset of CFS patients (Tanaka S, et al., 2003, Int J Mol Med 12:225-30), and higher levels of autoantibodies to insoluble cellular antigens were reported in CFS as compared to controls (von Mikeecz A., et al., 1997, Arthritis Rheum 40: 295-305).

However, there is no direct evidence with consistent data for the presence of pathogenic autoantibodies, or for T-lymphocyte-mediated autoimmunity. No indirect evidence has recreated the CFS disease in an animal model by immunization with antigens analogous to (putative) human autoantigens.

CFS is at present not defined as an autoimmune disease, and a recent protocol for a Cochrane review of pharmacological treatment in CFS states the aetiology as unknown. (Rawson K M, et al., 2007. Pharmacological treatments for chronic fatigue syndrome in adults. (Protocol) Cochrane Database of Systematic Reviews, Issue 4. Art. No.: CD006813.)

Other hypotheses for CFS pathogenesis are blood platelet dysfunction (Kennedy G, et al., 2006, Blood Coagul Fibrinolysis 17:89-92), neurological (Natelson B H, et al., 2005, Clin Diagn Lab Immunol 12:52-5), neuroendocrine (Van Den Eede F, et al., 2007, Neuropsychobiology 55:112-20), metabolic or autonomic disturbances, ion channel dysfunction (Chaudhuri A, et al., 2000, Med Hypotheses 54:59-63), zinc deficiency (Maes M, et al., 2006, J Affect Disord 90:141-7), toxin exposure or prior vaccinations (Appel S, et al., 2007, Autoimmunity 40:48-53). Others have focused on an abnormal response to exercise with intracellular immune deregulation as a possible mechanism in CFS pathogenesis (Nijs J, et al., 2004, Med Hypotheses 62:759-65). Also, post-infective impairment of the ability to synthesise n-3 and n-6 long-chain polyunsaturated fatty acids has been proposed as important in the pathophysiology of CFS (Puri B K. 2007, J Clin Pathol 60:122-4).

Hence, recent reviews on CFS in renown journals state that the disease at present has an unknown cause (Hampton T. 2006, Jama 296:2915; Hooper M. 2007, J Clin Pathol 60:466-71; Prins J B, et al., 2006, Lancet 367:346-55). Thus, no consistent picture has emerged for the aetiology and pathogenesis of CFS.

Current Treatment of CFS

Due to the lack of knowledge of the exact pathogenesis, and with no known causal mechanism, there is no current standard specific treatment for CFS. A systematic review concluded that CFS should be associated with a "biopsychosocial model" with emphasis on progressive muscular rehabilitation, combined with behavioural and cognitive treatment (Maquet et al, 2006, Ann Readapt Med Phys 49:337-47, 418-27).

The unknown aetiology of CFS is probably the reason for the remarkably few studies performed, evaluating therapy based upon a biological hypothesis.

As the majority of evidence suggests an immune system deregulation, perhaps precipitated by an exogenous stimulus, two studies have assessed use of intravenous gammaglobulin for CFS. One was a case report in three patients with CFS following an acute parvovirus B19 infection, treated with 5-days intravenous immunoglobulin, with improvement of clinical symptoms and resolution of cytokine dysregulation (Kerr et al, 2003, Clin Infect Dis 36:e100-6). In a double-blind, placebo-controlled, randomized study of 71 adolescents with CFS, three infusions of gammaglobulin were given one month apart, with functional improvement in the gammaglobulin-treated group at six-month follow-up with average duration 18 months. In the first six months of the trial, both the placebo group and the gammaglobulin-treated group reported improvement (Rowe 1997, J Psychiatr Res 31:133-47).

In a pilot study reported in abstract form (Lamprecht 2001, Meeting of the American association of chronic fatigue syndrome (AACFS). Seattle) six patients with CFS were given etanercept (Enbrel™, i.e. human tumor necrosis factor receptor p75 Fc fusion protein, which is a soluble competitive TNF-receptor acting to inhibit the TNF-mediated cellular response) and a clinical benefit was reported.

Among other therapeutic strategies, valganciclovir was used to treat 12 patients with long-standing fatigue and elevated antibody-titres to Epstein-Barr virus or human herpes virus-6, and nine had improvement of the symptoms, however with uncertainty as to whether the effects were mediated through anti-viral effect or through immunomodulation (Kogelnik A M,. 2006, J Clin Virol 37 Suppl 1:S33-8). Treatment with azithromycin, an antibiotic with immunomodulating properties, gave improvement in 59% of 99 CFS patients (Vermeulen & Scholte 2006, J Transl Med 4:34).

In a recent review of current research priorities in CFS (Kerr et al 2007, J Clin Pathol 60:113-6), new studies are encouraged to focus on the understanding of the molecular pathogenesis of the disease, to test useful biomarkers, and to aid in the development of specific treatment. Various molecular techniques are available and have been used for this purpose, including global gene expression analyses using microarrays.

Rituximab as an Example of B-Cell Depleting Antibodies in B-Cell Lymphoma and Autoimmunity Rituximab (Mabthera, RITUXAN®) is a monoclonal antibody directed against an epitope in the extracellular portion of the transmembrane molecule CD20. The antibody is a chimeric human-mouse in which the fragment antigen binding (Fab) part is mouse and the Fc-part is human. The CD20 protein is expressed on B-lymphocytes, but not on stem cells or on the mature plasma cells. CD20 is also expressed on the vast majority of B-cell lymphomas. CD20 is implicated in regulation of transmembrane calcium conductance and cell cycle progression, but the precise function is unknown (Janas et al 2005, Biochem Soc Symp:165-75). Upon binding of Rituximab to CD20, an immunological cell killing is mediated through the binding of complement to the Fc part with activation of the complement cascade, and also through activation antibody-dependent cellular cytotoxicity (ADCC) (Glennie et al 2007, Mol Immunol 44:3823-37).

The molecule does not internalize or shed from the plasma membrane after Rituximab binding, which allows the monoclonal antibody to persist on the cell surface to extend the immunological attack.

The role of Rituximab in treatment of B-cell lymphomas has emerged rapidly. Immunochemotherapy using Rituximab in combination with chemotherapy, or Rituximab monotherapy in indolent lymphomas, are now current standards of treatment, and has improved overall survival in the most common type of aggressive B-cell lymphomas (Diffuse large B-cell lymphoma), both in elderly (Coiffier et al 2002, N Engl J Med 346:235-42) and in younger patients (Pfreundschuh et al 2006, Lancet Oncol 7:379-91), and also in the most common indolent lymphoma (follicular lymphoma) (Marcus et al 2005, Blood 105:1417-23). In selected patients with follicular lymphoma, Rituximab is also used as maintenance treatment after induction therapy, with infusions every third month for two years, showing improved overall survival (van Oers et al 2006, Blood 108:3295-301).

In recent years, Rituximab was proved to be an effective treatment also in autoimmune diseases, where the B-cell depletion is often associated with a clinical improvement, e.g. in rheumatoid arthritis (Dass et al 2006, Expert Opin Pharmacother 7:2559-70). The list of different autoimmune diseases in which Rituximab has a therapeutic role is growing (Sanz et al 2007, Front Biosci 12:2546-67). For future B-cell targeting and depletion, the development of antibodies to specific B-cell subsets will be important (Dorner & Lipsky 2007, Expert Opin Biol Ther 7:1287-99).

The rituximab antibody is a genetically engineered chimeric murine/human monoclonal antibody directed against the CD20 antigen. Rituximab is the antibody called "C2B8" in U.S. Pat. No. 5,736,137. RITUXAN® is indicated for the treatment of patients with relapsed or refractory low-grade or follicular, CD20-positive, B cell non-Hodgkin's lymphoma. In vitro mechanism of action studies have demonstrated that RITUXAN® binds human complement and lyses lymphoid B cell lines through complement-dependent cytotoxicity (CDC) (Reff et al. Blood 83(2):435-445 (1994)). Additionally, it has significant activity in assays for antibody-dependent cellular cytotoxicity (ADCC). More recently, RITUXAN® has been shown to have antiproliferative effects in tritiated thymidine incorporation assays and to induce apoptosis directly, while other anti-CD19 and CD20 antibodies do not (Maloney et al Blood 88(10):637a (1996)). Synergy between RITUXAN® and chemotherapies and toxins has also been observed experimentally. In particular, RITUXAN® sensitizes drug-resistant human B cell lymphoma cell lines to the cytotoxic effects of doxorubicin, CDDP, VP-16, diphtheria toxin and ricin (Demidem et al Cancer Chemotherapy & Radiopharmaceuticals 12(3):177-186 (1997)). In vivo preclinical studies have shown that RITUXAN® depletes B cells from the peripheral blood, lymph nodes, and bone marrow of cynomolgus monkeys, presumably through complement and cell-mediated processes (Reff et al. Blood 83(2):435-445 (1994)). Patents and patent publications concerning CD20 antibodies include U.S. Pat. Nos. 5,776,456, 5,736,137, 5,843,439, 6,399,061, and 6,682,734, as well as US patent appln nos. US 2002/0197255A1, US 2003/0021781A1, US 2003/0082172 AI, US 2003/0095963 AI, US 2003/0147885 AI (Anderson et al); U.S. Pat. No. 6,455,043BI and WO00/09160 (Grillo-Lopez, A.); WO00/27428 (Grillo-Lopez and White); WO00/27433 (Grillo-Lopez and Leonard); WO00/44788 (Braslawsky et al); WO01/10462 (Rastetter, W.); WO01/10461 (Rastetter and White); WO01/10460 (White and Grillo-Lopez); US2001/0018041A1, US2003/0180292A1, WO01/34194 (Hanna and Hariharan); US appln no. US2002/0006404 and WO02/04021 (Hanna and Hariharan); US appln no. US2002/0012665 AI and WO01/74388 (Hanna, N.); US appln no. US 2002/0058029 AI (Hanna, N.); US appln no. US 2003/0103971 AI (Hariharan and Hanna); US appln no. US2002/0009444A1, and WO01/80884 (Grillo-Lopez, A); WO01/97858 (White, C); US appln no. US2002/0128488A1 and WO02/34790 (Reff, M.); WO02/060955 (Braslawsky et al.,); WO2/096948 (Braslawsky et al.); WO02/079255 (Reff and Davies); U.S. Pat. No. 6,171,586BI, and WO98/56418 (Lam et al); WO98/58964 (Raju, S.); WO99/22764 (Raju, S.); WO99/51642, U.S. Pat. No. 6,194,551BI, U.S. Pat. No. 6,242,195BI, U.S. Pat. No. 6,528,624BI and U.S. Pat. No. 6,538,124 (Idusogie et al); WO00/42072 (Presta, L.); WO00/67796 (Curd et al.); WO01/03734 (Grillo-Lopez et al.); US appln no. US 2002/0004587A1 and WO01/77342 (Miller and Presta); US appln no. US2002/0197256 (Grewal, L); US Appln no. US 2003/0157108 AI (Presta, L.); U.S. Pat. Nos. 6,565,827BI, 6,090,365BI, 6,287,537BI, 6,015,542, 5,843, 398, and 5,595,721, (Kaminski et al); U.S. Pat. Nos. 5,500, 362, 5,677,180, 5,721,108, 6,120,767, 6,652,852BI (Robinson et al); U.S. Pat. No. 6,410,391BI (Raubitschek et al); U.S. Pat. No. 6,224,866BI and WO00/20864 (Barbera-Guillem, E.); WO01/13945 (Barbera-Guillem, E.); WO00/67795 (Goldenberg); US Appl No. US 2003/0133930 AI and WO00/74718 (Goldenberg and Hansen); WO00/76542 (Golay et al.); WO01/72333 (Wolin and Rosenblatt); U.S. Pat. No. 6,368,596BI (Ghetie et al); U.S. Pat. No. 6,306,393 and US Appln no. US2002/0041847 AI, (Goldenberg, D.); US Appln no. US2003/0026801A1 (Weiner and Hartmann); WO02/102312 (Engleman, E.); US Patent Application No. 2003/0068664 (Albitar et al); WO03/002607 (Leung, S.); WO 03/049694, US2002/0009427A1, and US 2003/0185796 AI (Wolin et al); WO03/061694 (Sing and Siegall); US 2003/0219818 AI (Bohen et al); US 2003/0219433 AI and WO 03/068821 (Hansen et al.); US2003/0219818AI (Bohen et al); US2002/0136719A1 (Shenoy et al); WO2004/032828 (Wahl et al), each of which is expressly incorporated herein by reference. See, also, U.S. Pat. No. 5,849,898 and EP appln no. 330,191 (Seed et al); U.S. Pat. No. 4,861,579 and EP332, 865A2 (Meyer and Weiss); U.S. Pat. No. 4,861,579 (Meyer et al); WO95/03770 (Bhat et al); US 2003/0219433 AI (Hansen et al).

Safety Profile of Rituximab

The safety profile of Rituximab in treatment of B-cell lymphomas is well known, and based on experience from a database with 370 000 patients (Kavanaugh 2006, J Rheumatol Suppl 77:18-23). In lymphoma treatment, mild-to-moderate reaction during the first infusion is the most common side-effect, caused by cytokine release primarily in patients with a high initial tumor burden (Solal-Celigny 2006, Leuk Res 30 Suppl 1:S16-21). Allergic reactions may be seen during the infusion, due to the protein nature of the Rituximab molecule.

Concern with all B-cell directed therapy is the anticipated effects on humoral immunity. With extended treatment, and in particular with maintenance treatment, i.e. infusions every third month for two years (after induction therapy with perhaps 6-8 Rituximab-infusions every third week), the B-cell depletion is more pronounced and most patients will have hypogammaglobulinemia. However, the low levels of immunoglobulins and B-cell depletion do not seem to have a major impact on the clinical risk of infections.

One potential serious side-effect from use of Rituximab is the development of interstitial lung disease. This is a potentially life-threatening complication, but very rare with only 16 cases reported in the literature (Wagner et al 2007, Am J Hematol 82:916-9).

Safety issues related to Rituximab-treatment in chronic autoimmune diseases are exploited in clinical studies (Edwards et al 2006, Best Pract Res Clin Rheumatol 20:915-28), and with less time for follow-up so far. The long-term safety therefore remains to be clarified, especially when Rituximab is to be given once or twice yearly for many years. For patients with autoimmune diseases, Rituximab infusions are often given twice (a few weeks apart), and this sequence may be repeated after 6-12 months, i.e. considerably less doses than in lymphoma patients (in the short term).

Today a next generation of anti CD-20 antibodies able to deplete B-cells is used in clinical trials and will presumably be used in the clinical practice within the next years. For example, the fully humanized anti CD-20 antibody Ofatumomab of Glaxo-Smith-Kline is presently in clinical trials for B-cell lymphoma relapse. Fully humanized anti CD-20 antibody of the next generation are presumed to result in even more potent B-cell depletion, and should therefore be even more effective in the treatment of B-cell lymphomas than Rituximab. Further, it is presumed that they would display less site effects than described for Rituximab.

Various regimens for the treatment of chronic fatigue syndrome have been suggested. For example, in US 2007/025375 a complex treatment scheme is provided for the treatment of patient suffering from chronic fatigue syndrome. Said region comprises inter alia the administration of milnacipran.

In view of the unknown aetiology of CFS/ME (myalgic encephalomyelitis) there is a continued demand for compounds useful for an effective treatment of CFS.

BRIEF DESCRIPTION OF THE PRESENT INVENTION

The present invention aims in providing new compounds applicable in the treatment of chronic fatigue syndrome. In particular, the inventors have found that B-cell depleting agents, like anti-CD20 antibodies, are useful in the treatment of chronic fatigue syndrome.

Preferably, the anti-CD20 antibodies or CD20-binding antibody fragments thereof are monoclonal antibodies. Particular preferred, said monoclonal antibodies are humanized antibodies when administered to human subjects. It is also contemplated in the present invention that the antibodies may be present as antibody fragments which may e.g. be produced recombinantly by genetic engineering.

In a further aspect, the present invention relates to methods for the treatment of chronic fatigue syndrome/myalgic encephalomyelitis comprising the step of administering a therapeutically effective amount of a B-cell depleting agent, e.g. a B-cell depleting anti-CD20 antibody or a CD20-binding to a subject afflicted with said disease or disorder.

BRIEF DESCRIPTION OF THE DRAWING

FIG. 1 shows graphically the development of CFS symptoms for three patients over a one year period outlining the different interventions, namely Rituximab® or Methotrexat (M). The symptom score of CFS symptoms which is in a range of 0 to 10 wherein 0 means no symptoms while 10 refers to very severe symptoms of CFS.

DETAILED DESCRIPTION OF THE INVENTION

The present invention concerns B-cell depleting agents either B-cell depleting biological entities, like anti-CD20 antibodies or CD20-binding antibody fragments thereof or chemical entities, like small molecules having a B-cell depleting activity for the treatment of chronic fatigue syndrome/myalgic encephalomyelitis.

In the context of the present invention, the terms "chronic fatigue syndrome (CFS" and "myalgic encephalomyelitis (ME)" are used synonymously.

As used herein, the term "B-cell depletion" or "B-cell depleting activity" refers to the ability of the entity, either a chemical or biological entity, e.g. an antibody, to reduce circulating B-cell levels in a subject. B-cell depletion may be achieved e.g. by inducing cell death or reducing proliferation.

The "CD20" antigen, or "CD20," is an about 35-kDa, non-glycosylated phosphoprotein found on the surface of greater than 90% of B cells from peripheral blood or lymphoid organs in humans. CD20 is present on both normal B cells as well as malignant B cells, but is not expressed on stem cells. Other names for CD20 in the literature include "B-lymphocyte-restricted antigen" and "Bp35". The CD20 antigen is described in Clark et al. Proc. Natl. Acad. Sd. (USA) 82:1766 (1985), for example. The term CD20 includes the equivalent molecules of other species than human. Recently, low level expression of CD20 on a subset of T-cells and NK-cells has been reported.

A "B-cell" is a lymphocyte that matures within the bone marrow, and includes a naive B cell, memory B cell, or effector B cell (plasma cells).

In a broader sense, the present invention relates not only to the use of antibodies or fragments thereof for the treatment of CFS but to the use of antagonists of the CD20 molecule in general having a B-cell depleting activity for the treatment of CFS.

An "antagonist" or "B-cell depleting agent" which is used herein interchangeably is a molecule which, e.g. upon binding to a B cell surface marker, like CD20 on B cells, destroys or depletes B cells in a mammal and/or interferes with one or more B cell functions, e.g. by reducing or preventing a humoral response elicited by the B cell. The antagonist or B-cell depleting agent according to the present invention is able to deplete B cells (i.e. reduce circulating B cell levels) in a mammal treated therewith. Such depletion may be achieved via various mechanisms such antibody-dependent cell-mediated cytotoxicity (ADCC) and/or complement dependent cytotoxicity (CDC), inhibition of B cell proliferation and/or induction of B cell death (e.g. via apoptosis). Antagonists included within the scope of the present invention include antibodies, synthetic or native sequence peptides and small molecule antagonists which bind to the B cell surface marker, optionally conjugated with or fused to a cytotoxic agent. A preferred antagonist is a CD20 antibody or CD20-binding antibody fragment. Furthermore, small molecule antagonists are preferred, like the known B-cell depleting agent Methotrexat.

Insofar that other cells than B-cells express the CD20 antigen like a subset of T-cells or NK-cells, these cells are also depleted with the B-cells depleting agent being an agent acting via CD20.

Antagonists which "induce apoptosis" are those which induce programmed cell death, e.g. of a B cell, as determined by standard apoptosis assays, such as binding of annexin V, fragmentation of DNA, cell shrinkage, dilation of endoplasmic reticulum, cell fragmentation, and/or formation of membrane vesicles (called apoptotic bodies).

The term "antibody" herein is used in the broadest sense and specifically covers monoclonal antibodies, polyclonal antibodies, multispecific antibodies {e.g. bispecific antibodies) formed from at least two intact antibodies, and antibody fragments so long as they exhibit the desired biological activity.

In a preferred embodiment, the antibody useful for the treatment of CFS is a B-cell depleting CD20-binding antibody fragment.

"CD20-binding antibody fragments" comprise a portion of an intact antibody which comprises the antigen binding region thereof. Examples of antibody fragments include Fab, Fab', F(ab')2, and Fv fragments; diabodies; linear antibodies; single-chain antibody molecules; and multispecific antibodies formed from antibody fragments. For the purposes herein, an "intact antibody" is one comprising heavy and light variable domains as well as an Fc region.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (V11) followed by a number of constant domains. Each light chain has a variable domain at one end (V1) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervaiiable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et ah, Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known. The "light chains" of antibodies (immunoglobulins) from any vertebrate species can be assigned to one of two clearly distinct types, called kappa (K) and lambda (λ), based on the amino acid sequences of their constant domains. Depending on the amino acid sequence of the constant domain of their heavy chains, antibodies can be assigned to different classes. There are five major classes of intact antibodies: IgA5 IgD, IgE, IgG, and IgM, and several of these maybe further divided into subclasses (isotypes), e.g., IgG1, IgG2, IgG3, IgG4, IgA, and IgA2. The heavy chain constant domains that correspond to the different classes of antibodies are called a, δ, e, γ, and μ, respectively. The subunit structures and three-dimensional configurations of different classes of immunoglobulins are well known. "Single-chain Fv" or "scFv" antibody fragments comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. For a review of scFv see Plückthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain (V11) connected to a light chain variable domain (V1) in the same polypeptide chain (VH-V1). By using a linker that is too short to allow pairing between the two domains on the same chain, the domains are forced to pair with the complementary domains of another chain and create two antigen-binding sites. Diabodies are described more fully in, for example, EP 404097; WO 93/11161; and Hollinger et al, Proc. Natl. Acad. Sd. USA, 90:6444-6448 (1993).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al, Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature, 352:624-628 (1991) and Marks et al, J. Mol Biol, 222:581-597 (1991), for example. The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al, Proc. Natl. Acad. Sd. USA, 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780). "Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al, Nature 321:522-525 (1986); Riechmann et al, Nature 332: 323-329 (1988); and Presta, Curr. Op. Struct. Biol. 2:593-596 (1992). The term "hypervariable region" when used herein refers to the amino acid residues of an antibody which are responsible for antigen-binding. The hypervariable region comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al, Sequences of Proteins of Immunological Interest, 5th Ed. Public Health Service, National Institutes of Health, Bethesda, Md. (1991)) and/or those residues from a "hypervariable loop" {e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined. A "naked antibody" is an antibody (as herein defined) which is not conjugated to a heterologous molecule, such as a cytotoxic moiety or radiolabel. Examples of antibodies which bind the CD20 antigen include: "C2B8" which is now called "Rituximab" ("RITUXAN®") (U.S. Pat. No. 5,736,137, expressly incorporated herein by reference); the yttrium-[90]-labeled 2B8 murine antibody designated "Y2B8" or "Ibritumomab Tiuxetan" ZEVALIN® (U.S. Pat. No. 5,736,137, expressly incorporated herein by reference); murine IgG2a "BI," also called "Tositumomab," optionally labeled with 131I to generate the "131I-BI" antibody (iodine 1131 tositumomab, BEXXAR™) (U.S. Pat. No. 5,595,721, expressly incorporated herein by reference); murine monoclonal antibody "1F5" (Press et al. Blood 69(2):584-591 (1987) and variants thereof including "framework patched" or humanized 1F5 (WO03/002607, Leung, S.; ATCC deposit HB-96450); murine 2H7 and chimeric 2H7 antibody (U.S. Pat. No. 5,677, 180, expressly incorporated herein by reference); humanized 2H7; Ofatumumab, a fully humanized IgG1 against a novel epitope on CD20 huMax-CD20 (Genmab, Denmark; WO2004/035607); AME-133 (Applied Molecular Evolution); A20 antibody or variants thereof such as chimeric or humanized A20 antibody (cA20, hA20, respectively) (US 2003/0219433, Immunomedics); and monoclonal antibodies L27, G28-2, 93-1B3, B—Cl or NU-B2 available from the International Leukocyte Typing Workshop (Valentine et ah, In: Leukocyte Typing III (McMichael, Ed., p. 440, Oxford University Press (1987)). Further, suitable antibodies are e.g. Ocrelizumab, a fully humanized anti-CD20 antibody of Biogen Idec/Genentech/Roche the antibody GA101, a third generation humanized anti-CD20-antibody of Biogen Idec/Genentech/Roche. Moreover, BLX-301 of Biolex Therapeutics, a humanized anti CD20 with optimized glycosyylation or Veltuzumab (hA20) of Immunomedics or DXL625 of Inexus Biotechnology both are humanized anti-CD20 antibodies are suitable.

Moreover, it is assumed that other B-cell depleting agents, in particular, anti-CD22 antibodies, like Epratuzumab or anti-CD19 humanized antibodies, like MDX-1342 can be used for the treatment of CFS.

The terms "rituximab" or "RITUXAN®" or "mabthera" herein refer to the genetically engineered chimeric murine/human monoclonal antibody directed against the CD20 antigen and designated "C2B8" in U.S. Pat. No. 5,736,137, expressly incorporated herein by reference, including fragments thereof which retain the ability to bind CD20. Purely for the purposes herein and unless indicated otherwise, "humanized 2H7" refers to a humanized antibody that binds human CD20, or an antigen-binding fragment thereof, wherein the antibody is effective to deplete primate B cells in vivo.

The expression "effective amount" of the B-cell depleting agent or antagonist, in particular of the anti-CD20 antibody or CD20-binding antibody fragment thereof, refers to an amount of the B-cell depleting agent or antagonist which is effective for treating CFS. For example, the anti-CD20 antibody for the treatment of chronic fatigue syndrome/myalgic encephalomyelitis is administered in the range of 10 mg to 5000 mg per dosage. For example, the dosage may be in the range of from 100 to 1000 mg/m2, in particular, 500 mg/m2 as a single infusion for Rituximab. Typically, the dosage for Methotrexate is in the range of 5 mg to 30 mg per week.

In one preferred embodiment, the B-cell depleting agent is a chemical entity, e.g. a small molecule. A variety of B-cell depleting agents are known in the art for example known B-cell depleting agents are BAFF-antagonists. Furthermore, known B-cell depleting agents include antagonist of BR3, agonists of alpha-4-integrins etc. For example, Methotrexate is an analogue of folic acid displaying B-cell depleting activity. Other useful B-cell depleting agent are small modular immunopharmaceuticals (SMIP) against CD20. For example, SMIP acting as B-cell depleting agents are TRU-015 or SBI-087 of Trubion Pharmaceuticals. Also, SMIP can be single chain polypeptides, smaller than antibodies, having a potent B-cell depletion activity.

In a preferred embodiment, a combination of an anti CD20 antibody and representing a biological entity of a B-cell depleting agent and Methotrexat, representing a chemical entity of a B-cell depleting agent, are used for treating chronic fatigue syndrome of myalgic encephalomyelitis. Administration of these entities may be effected simultaneously, separately or sequentially. For example, in a first regimen either the antibody or Methotrexat is administered to the subject while in a second regimen the other agent is administered.

The composition comprising the B-cell depleting agent, the antagonist, in particular, the anti CD20 antibody or the CD20-binding antibody fragment thereof, will be formulated, dosed, and administered in a fashion consistent with good medical practice. Factors for consideration in this context include the stage of the particular disease or disorder being treated, the particular mammal being treated, the clinical condition of the individual subject, the site of delivery of the agent, the method of administration, the scheduling of administration, and other factors known to medical practitioners. The effective amount of the B-cell depleting agent, like an antibody or antibody fragment to be administered will be governed by such considerations. As a general proposition, the effective amount of the antagonist administered parenterally per dose will be in the range of about 20 mg/m2 to about 10,000 mg/m2 of subject body, by one or more dosages. Exemplary dosage regimens for intact antibodies include 375 mg/m2 weekly×4; 1000 mg×2 (e.g. on days 1 and 15); or 1 gram×3. The antibody for the administration to a subject in a single therapeutically effective dosage of said antibody is of 50 to 2000 mg/m2 or multiple of therapeutically effective dosages of said antibody or CD20-binding antibody fragment thereof of 50 to 2000 mg/m2. As noted above, however, these suggested amounts of antibody are subject to a great deal of therapeutic discretion. The key factor in selecting an appropriate dose and scheduling is the result obtained, as indicated above. The B-cell depleting agent antagonist, like the antibody, is administered by any suitable means, including parenteral, topical, subcutaneous, intraperitoneal, intrapulmonary, intranasal, and/or intralesional administration. Parenteral infusions include intramuscular, intravenous, intraarterial, intraperitoneal, or subcutaneous administration. Intrathecal administration is also contemplated. In addition, the B-cell depleting agent antagonist, like the antibody may suitably be administered by pulse infusion, e.g., with declining doses of the antagonist. Preferably the dosing is given by intravenous injections.

Methods for generating such B-cell depleting antagonists will be described here. The antigen to be used for production of, or screening for, antagonist(s) maybe, e.g., a soluble form of CD20 or a portion thereof, containing the desired epitope. Alternatively, or additionally, cells expressing CD20 at their cell surface can be used to generate, or screen for, antagonist (s). Other forms of CD20 useful for generating antagonists will be apparent to those skilled in the art.

While the preferred antagonist is an antibody, antagonists other than antibodies are contemplated herein. For example, the antagonist may comprise a small molecule antagonist. Libraries of small molecules may be screened against CD20 in order to identify a small molecule which binds to that antigen. Alternatively, the small molecules may be screened on their B-cell depleting activity in general by known techniques. The small molecule may further be screened for its antagonistic properties. The antagonist may also be a peptide generated by rational design or by phage display (see, e.g., WO98/35036 published 13 Aug. 1998). In one embodiment, the molecule of choice maybe a "CDR mimic" or antibody analogue designed based on the CDRs of an antibody. While such peptides may be antagonistic by themselves, the peptide may optionally be fused to a cytotoxic agent so as to add or enhance antagonistic properties of the peptide. A description follows as to exemplary techniques for the production of the antibody antagonists used in accordance with the present invention.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl2, or R1N=C=NR, where R and R1 are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ¹/₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies. For example, the monoclonal antibodies may be made using the hybridoma method first described by Kohler et ah, Nature, 256:495 (1975), or may be made by recombinant DNA methods (U.S. Pat. No. 4,816,567).

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et ah, Curr. Opinion in Immunol., 5:256-262 (1993) and Pluckthun, Immunol. Revs., 130: 151-188 (1992). In a further embodiment, antibodies or antibody fragments can be isolated from antibody phage libraries generated using the techniques described in McCafferty et ah, Nature, 348:552-554 (1990). Clackson et ah, Nature, 352:624-628 (1991) and Marks et ah, J. Mol. Biol., 222:581-597 (1991) describe the isolation of murine and human antibodies, respectively, using phage libraries. Subsequent publications describe the production of high affinity (nM range) human antibodies by chain shuffling (Marks et ah, Bio/Technology, 10:779-783 (1992)), as well as combinatorial infection and in vivo recombination as a strategy for constructing very large phage libraries (Waterhouse et ah, Nuc. Acids. Res., 21:2265-2266 (1993)). Thus, these techniques are viable alternatives to traditional monoclonal antibody hybridoma techniques for isolation of monoclonal antibodies. The DNA also may be modified, for example, by substituting the coding sequence for human heavy- and light chain constant domains in place of the homologous murine sequences (U.S. Pat. No. 4,816,567; Morrison, et ah, Proc. Natl. Acad. ScL USA, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al, Nature, 321:522-525 (1986); Riechmann et al, Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species, hi practice, humanized antibodies are typically human antibodies in which some hypervariable region residues and possibly some FR residues are substituted by residues from analogous sites in rodent antibodies. The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al, J. Immunol, 151:2296 (1993); Chothia et al, J. Mol. Biol, 196:901 (1987)). Another method uses a particular framework region derived from the consensus sequence of all human antibodies of a particular subgroup of light or heavy chain variable regions. The same framework may be used for several different humanized antibodies (Carter et al, Proc. Natl. Acad. ScL USA, 89:4285 (1992); Presta et al, J. Immunol, 151:2623 (1993)). It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(iv) Human Antibodies

As an alternative to humanization, human antibodies can be generated. For example, it is now possible to produce transgenic animals {e.g., mice) that are capable, upon immunization, of producing a full repertoire of human antibodies in the absence of endogenous immunoglobulin production. For example, it has been described that the homozygous deletion of the antibody heavy chain joining region (J11) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al, Proc. Natl. Acad. ScL USA, 90:2551 (1993); Jakobovits et al, Nature, 362:255-258 (1993); Bruggermann et al, Year in Immuno., 7:33 (1993); and U.S. Pat. Nos. 5,591,669, 5,589, 369 and 5,545,807. Alternatively, phage display technology (McCafferty et al, Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as MI 3 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al, Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al, EMBO J. 12:725-734 (1993). See, also, U.S. Pat. Nos.

5,565,332 and 5,573,905. Human antibodies may also be generated by in vitro activated B cells (see U.S. Pat. Nos. 5,567,610 and 5,229,275).

(v) Antibody Fragments

Various techniques have been developed for the production of antibody fragments. Traditionally, these fragments were derived via proteolytic digestion of intact antibodies (see, e.g., Morimoto et al, Journal of Biochemical and Biophysical Methods 24:107-117 (1992) and Brennan et al, Science, 229: 81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')2 fragments (Carter et al, Bio/Technology 10:163-167 (1992)). According to another approach, F(ab')2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

Pharmaceutical Formulations

Therapeutic formulations of the B-cell depleting agents, like antibodies or other antagonists used in accordance with the present invention are prepared for storage by mixing an antibody or a fragment thereof having the desired degree of purity with optional pharmaceutically acceptable carriers, excipients or stabilizers {Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Exemplary anti-CD20 antibody formulations are described in WO98/56418, expressly incorporated herein by reference. This publication describes a liquid multidose formulation comprising 40 mg/mL rituximab, 25 mM acetate, 150 mM trehalose, 0.9% benzyl alcohol, 0.02% polysorbate 20 at pH 5.0 that has a minimum shelf life of two years storage at 2-8° C. Another anti-CD20 formulation of interest comprises 1 mg/mL rituximab in 9.0 mg/mL sodium chloride, 7.35 mg/mL sodium citrate dihydrate, 0.7 mg/mL polysorbate 80, and Sterile Water for Injection, pH 6.5. Lyophilized formulations adapted for subcutaneous administration are described in U.S. Pat. No. 6,267,958 (Andya et ah). Such lyophilized formulations may be reconstituted with a suitable diluent to a high protein concentration and the reconstituted formulation may be administered subcutaneously to the mammal to be treated herein. Crystallized forms of the antibody or antagonist are also contemplated. See, for example, US 2002/0136719AI.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980). Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ? ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydiOxybutyric acid. The formulations to be used for in vivo administration must be sterile. This is readily accomplished by filtration through sterile filtration membranes.

EXAMPLES

At the Department of Oncology and Medical Physics, Haukeland University Hospital, a striking symptomatic improvement after cytotoxic chemotherapy in a 43-year old female patient with stable CFS (debut in 1997, preceded by Epstein-Barr infection), was observed. She developed Hodgkin's disease in 2003, and was treated with chemotherapy and radiation. She had a lymphoma relapse in 2004, and was treated with chemotherapy. Contrary to the expected (CFS patients generally tolerate all types of drugs and stress poorly), the patient experienced a marked decrease in CFS symptoms during and after this chemotherapy. The changes were not interpreted as related to lymphoma activity, and the effects lasted for approximately 5 months after chemotherapy initiation, with then gradual relapse of CFS-like symptoms. In addition to the cytotoxic effects, the chemotherapeutics given also had an immunomodulatory effect. It is assumed that the effects on CFS symptoms are mediated mainly through the drug Methotrexate administered during chemotherapy.

When reviewing the literature on CFS in an attempt to understand what our patient encountered during and after cancer chemotherapy, the conclusion was done that modification of the immune system seemed a likely explanation of the marked, but transient symptom improvement experienced. It may well be that chronic B-cell activation seen in CFS patients is important for the symptoms and also physiological changes reported, such as central nervous blood circulation alterations, and reports of lymphocyte infiltration in brain tissue, spinal nerve roots or cardiac muscle.

Possible modes of action of B-cell depletion could be at several sites, such as interactions with the T-cell system, thus modifying inflammatory processes, and in influencing the levels of important pleiotropic players in the immune homeostasis, such as the vasoactive neuropeptides. These have a wide range of activities in the central nervous system.

Taking these existing data into account, together with the unexpected improvement of fatigue and pain in the CFS patient after immunomodulatory cytotoxic therapy, it is assumed that B-cell depletion as a concept could allow treatment of CFS.

At present, achievement of B-cell depletion is most readily achieved by the use of the monoclonal anti-CD20 antibody Rituximab. However, also new generation anti-CD20 antibodies are supposed to have at least a similar effect on CFS symptoms, due to a presumed more potent B-cell depletion achieved.

Pilot Patient 1:

As a first pilot patient, the above-mentioned woman received Rituximab 500 mg/m$^2$ as a single infusion after informing of the experimental nature of the procedure and the risks involved. Prior to treatment, she had a stable CFS with marked fatigue and she was not able to work out-of-house or do house-keeping. She used an electrical wheel-chair for outdoor movement. Starting between five and six weeks after the infusion, she experienced a marked improvement in symptoms, with profoundly less fatigue, decreasing muscle pain, decreasing burning pain in the skin, and declining headaches, accompanied with a diminishing need of opioid analgesics. Due to declined fatigue, she could now go for long walks, resumed her hobbies and was able to do house-keeping work and take care of her children. She also reported a marked improvement in cognitive function, retaining the ability to concentrate, and was again able to read and e.g. work with computers. The effect after the first infusion lasted until 14 weeks after the Rituximab infusion, then declined, with a gradual, but not complete relapse of CFS symptoms.

Five months after the first Rituximab infusion, she again had stable and disabling CFS symptoms. She received a new single infusion of Rituximab in the same dosage. After 6 weeks, she again experienced a gradual and major recovery from all CFS symptoms (fatigue, pain, cognitive symptoms) with a major effect on the quality of life. After the second infusion (also as a single infusion at a low dose 500 mg/m$^2$), the therapeutic effect lasted until 16 weeks, with then slowly and gradual symptom worsening thereafter.

It was then decided to start weekly oral low-dose Methotrexate from 18 weeks after the second Rituximab-infusion, starting at 7.5 mg per week, and increasing the dose to 12.5 mg per week during the next two months. From 12 weeks after onset of weekly Mtx, she has again experienced gradual and moderate CFS symptom recovery. She has now used Mtx for 22 weeks, and she interprets the improvement to be moderate and significant, but at present not as pronounced and rapid as after Rituximab treatment. However she still experiences a gradual improvement in her condition. The development of CFS symptoms is shown in FIG. 1.

Pilot Patient 2:

He is a 42-year old male, and developed CFS after an Epstein-Barr infection 8 years ago. He had marked fatigue and was not able to do any work since encountering the entity. He was constrained to sit in a chair most of the days. After mild exercise he had major problems with exhaustion, increasing muscle pain and headaches. He also had fever sensations, sweating and diarrhoea. He had serious cognitive disturbances. Although being a previous experienced computer engineer, he was unable to use a computer or to read coherently more than 1-2 pages in a book.

He was given a single infusion of Rituximab 500 mg/m$^2$. The first symptom to improve (3 weeks after infusion) was the longstanding diarrhea. Starting 6 weeks after infusion, he experiences a marked response with a dramatic improvement in fatigue, pain, cognitive and autonomic symptoms. He was then able to perform manual labour and enjoy computer games and reading. After the relatively low dose (single infusion 1000 mg) the effect was most prominent until 12 weeks, and thereafter gradually declined. He and his family described the clinical improvement as significant, yielding a major impact on the quality of life of the whole family.

Five months after the first Rituximab infusion, he has now been retreated with two infusions of Rituximab 1000 mg two weeks apart. As following the first treatment, he started to recover first from the diarrhea (after 3 weeks). Then, after 6 weeks, he reported less cognitive symptoms, and some days later the fatigue started to improve.

The double Rituximab infusion gave a clear CFS symptom improvement most prominent 16 weeks after the infusion. Thereafter, he has experienced a very slow and gradual increase in his symptoms. However, 5 months after the infusion, he still has a clinical response (he is still better than his condition prior to treatment) (FIG. 1). He has now started weekly oral low-dose Methotrexate treatment.

Pilot Patient 3:

She is a 22-year student, developing CFS after mononucleosis 7 years ago. Initially, she had the full-blown clinical picture with marked fatigue, with pain including headaches, cognitive disturbances and autonomic symptoms. During the last four years, she had however experienced some improvement, but still retained marked fatigue, excess sleep requirement and loose bowels. She had moderate cognitive disturbances and moderate muscle pain.

She was given a single infusion of Rituximab 500 mg/m$^2$. This patient also experienced improvement from loose bowels 3 weeks after infusion. Six weeks after infusion, she noted some improvement in muscle pain. The first five months, she also had slight improvement in fatigue, but transient and of shorter duration than in the other patients.

However, from 6 months after the infusion, she experienced a major clinical response on all CFS symptoms, to a high level of functioning not experienced the last 7 years. She started to study full-time, and could read without problems, and also noted a marked improvement in her short-time memory. This dramatic improvement has now lasted for 4½ months. The following weeks she then experienced a gradual relapse of CFS symptoms. She has now received new infusions of Rituximab (two infusions 500 mg/m$^2$, given two weeks apart).

Methotrexat (Mtx) is a therapeutic agent with known (but not well understood) immunomodulatory properties. Given orally on a weekly schedule for rheumatoid arthritis, one of the drug effects is a moderate B-cell depletion, which mechanistically is similar to but not as pronounced as the effect of Rituximab (Edwards et al. NEJM, 2004. Efficacy of B-Cell Targeting Therapy with Rituximab in Patients with Rheumatoid Arthritis). For one of the three pilot patients (patient 1), she was treated weekly with Methotrexat for the last 22 weeks, also with a significant and moderate clinical response on CFS symptoms, starting from 10 weeks after initiating Mtx.

In conclusion, a major clinical response after Rituximab treatment in three out of three pilot patients, in two these with a repeated clinical responses also after a second Rituximab treatment, has been observed.

The third had a limited improvement in CFS symptoms from 6 weeks after the Rituximab infusion. However, from 6 to 10½ months after the infusion she had a major clinical response on all CFS related symptoms lasting until now (10½ months after infusion). Then she had a gradual relapse, and she has now received new Rituximab treatment (two infusions, i.e. at weeks 47 and 49 after her first Rituximab treatment).

All five treatments of the three patients resulted in marked to moderate main symptom improvement. For these three patients, the kinetics in symptom improvement has been very similar, but with in addition a major late and long-lasting response in patient 3, as shown in FIG. 1. The interval is compatible with the known degradation and half-time of certain proteins that can be produced by B-lymphocytes. The reappearance of symptoms after Rituximab treatment is compatible with the maturing of pre-plasma cell B-lymphocytes from stem cells after the CD20 antigen directed B-cell lysis, which is mediated through complement-directed cytotoxicity (CDC) and by antibody dependent cellular cytotoxicity (ADCC). These immature B-cells have been shown to be capable of protein production, among them the production of antibodies.

The invention claimed is:

1. A method of treating chronic fatigue syndrome and optionally myalgic encephalomyelitis comprising the step of administering a B-cell depleting agent to a subject afflicted therewith.

2. The method for treating chronic fatigue syndrome and myalgic encephalomyelitis as recited in claim 1 wherein said step of administering includes providing said B-cell depleting agent to said subject afflicted therewith one or two infusions twice within two weeks.

3. The method of treating chronic fatigue syndrome and myalgic encephalomyelitis according to claim 1 wherein said B-cell depleting agent is a B-cell depleting anti CD20 antibody or CD20-binding antibody fragment thereof, and wherein Methotrexate is administered simultaneously, separately or sequentially with said B-cell depleting anti CD20 antibody or CD20-binding antibody fragment thereof to said subject.

4. The method of treating chronic fatigue syndrome and myalgic encephalomyelitis according to claim 2 wherein said B-cell depleting agent is a B-cell depleting anti CD20 antibody or CD20-binding antibody fragment thereof, and wherein Methotrexate is administered simultaneously, separately or sequentially with said B-cell depleting anti CD20 antibody or CD20-binding antibody fragment thereof to said subject.

5. The method of treating chronic fatigue syndrome and myalgic encephalomyelitis according to claim 1, wherein said B-cell depleting agent is a B-cell depleting anti CD20 antibody or CD20-binding antibody fragment thereof.

6. The method of treating chronic fatigue syndrome and myalgic encephalomyelitis according to claim 5, wherein said B-cell depleting anti CD20 antibody or CD20-binding antibody fragment thereof is a monoclonal antibody or CD20-binding antibody fragment thereof.

7. The method of treating chronic fatigue syndrome and myalgic encephalomyelitis according to claim 5, wherein said B-cell depleting anti CD20 antibody or CD20-binding antibody fragment thereof is a humanized anti CD20 antibody or CD20-binding antibody fragment thereof.

8. The method of treating chronic fatigue syndrome and myalgic encephalomyelitis according to claim 5, wherein said B-cell depleting anti CD20 antibody or CD20-binding antibody fragment thereof is a B-cell depleting CD20 antibody fragment binding to CD20.

9. The method of treating chronic fatigue syndrome and myalgic encephalomyelitis according to claim 8, wherein said B-cell depleting CD20 antibody fragment is selected from the group consisting of F(ab')$_2$, F(ab'), Fab, Fv and sFv.

10. The method of treating chronic fatigue syndrome and myalgic encephalomyelitis according to claim 1, wherein said B-cell depleting agent is selected from the group consisting of Rituximab. Ofatumumab, Ocrelizumab, GA101, BCX-301, Veltuzumab, and DXL 625.

11. The method of treating chronic fatigue syndrome and myalgic encephalomyelitis according to claim 1, wherein said B-cell depleting agent is Rituximab.

12. The method of treating chronic fatigue syndrome and myalgic encephalomyelitis according to claim 1, wherein said B-cell depleting agent is Methotrexate TRU-015 or SBI-087.

13. The method of treating chronic fatigue syndrome and myalgic encephalomyelitis according to claim 5, wherein said B-cell depleting anti CD20 antibody or CD20-binding antibody fragment thereof is administered in an amount in the range of 10 mg to 5000 mg per dosage.

14. The method of treating chronic fatigue syndrome and myalgic encephalomyelitis according to claim 5, wherein said B-cell depleting anti CD20 antibody or CD20-binding antibody fragment thereof is administered to said subject in a single therapeutically effective dosage of said antibody of 50 to 2000 mg/m$^2$ or multiple of therapeutically effective dosages of said anti CD20 antibody or anti CD20-binding antibody fragment thereof of 50 to 2000 mg/m$^2$.

* * * * *

UNITED STATES PATENT AND TRADEMARK OFFICE
CERTIFICATE OF CORRECTION

| | | |
|---|---|---|
| PATENT NO. | : 7,914,785 B2 | Page 1 of 1 |
| APPLICATION NO. | : 12/348024 | |
| DATED | : March 29, 2011 | |
| INVENTOR(S) | : Olav Mella et al. | |

It is certified that error appears in the above-identified patent and that said Letters Patent is hereby corrected as shown below:

On the Title page, please add:

Related U.S. Application Data

(60) Provisional application No. 61/018,551, filed on Jan. 2, 2008

Signed and Sealed this
Seventh Day of June, 2011

David J. Kappos
*Director of the United States Patent and Trademark Office*